United States Patent [19]

Dailey, Jr.

[11] Patent Number: 4,723,038

[45] Date of Patent: Feb. 2, 1988

[54] PROCESS FOR PREPARING SEED GERMINATING STIMULANTS

[75] Inventor: Oliver D. Dailey, Jr., Metairie, La.

[73] Assignee: The United States of America as represented by the Secretary of Agriculture, Washington, D.C.

[21] Appl. No.: 814,944

[22] Filed: Dec. 31, 1985

[51] Int. Cl.$^4$ ............................................. C07C 61/28
[52] U.S. Cl. ..................................... 562/501; 549/11; 549/15; 549/32; 549/525; 549/546; 560/125; 560/126; 560/128
[58] Field of Search ...................... 560/126, 128, 119; 549/546, 525; 562/501

[56] References Cited

U.S. PATENT DOCUMENTS

| | | | |
|---|---|---|---|
| 2,794,812 | 6/1957 | Phillips | 549/546 |
| 3,887,547 | 6/1975 | Sih | 260/24 R |
| 3,887,625 | 6/1975 | Schulte-Elte | 560/128 |
| 3,890,370 | 6/1975 | Buchi | 560/128 |
| 4,259,512 | 3/1981 | Dolby | 560/126 |

OTHER PUBLICATIONS

Brooks, J. Org. Chem., 48, pp. 277–278 (1983).
Brooks, D. W., et al., Practical Total Synthesis of (±)-Strigol. Journal of Organic Chemistry, vol. 50, pp. 628–632, Mar. 8, 1985.

*Primary Examiner*—Michael L. Shippen
*Attorney, Agent, or Firm*—M. Howard Silverstein; David G. McConnell; Raymond C. Von Bodungen

[57] ABSTRACT

Processes for preparing compounds which exhibit seed germinating activity are disclosed. An ester of acetoacetic acid is condensed with a ketone to produce a substituted cyclohexenone which is reacted with a thiol to get a dithioketal which is then desulfurized to produce an ester of a substituted cyclohex-2-ene-1-carboxylic acid which exhibits seed germinating activity. The same compound can be produced by a different process which reacts the substituted cyclohexenone with a reducing agent. An exemplary reducing agent would be an organosilane and a Lewis acid.

22 Claims, No Drawings

PROCESS FOR PREPARING SEED GERMINATING STIMULANTS

BACKGROUND OF THE INVENTION (1) Field of the Invention

This invention relates to processes for producing seed germination stimulants.

(2) Description of the Prior Art

C. J. Sih, U.S. Pat. No. 3,887,547 discloses a process for preparing (±)-strigol, a potent seed germinating stimulant.

D. W. Brooks (J. Org Chem, 50, p. 628, 1985) teaches an improved method over C. J. Sih for making strigol.

Both methods for making (±)-strigol utilize very expensive chemical reagents and require complex organic synthesis.

SUMMARY OF THE INVENTION

A process for preparing compounds which exhibit seed germinating activity is disclosed and comprises the following steps in combination: An ester of acetoacetic acid is condensed with a ketone to produce a substituted cyclohexenone which is reacted with a thiol to produce a dithioketal. This dithioketal is then desulfurized to produce an ester of a substituted cyclohex-2-ene-1-carboxylic acid which exhibits seed germinating activity. This same compound can be produced by a different process which comprises reacting the substituted cyclohexenone with a satisfactory reducing agent. The reducing agent comprises an organosilane and a Lewis acid.

In addition the following new compounds are also disclosed: ethyl 2,6,6-trimethylcyclohex-2-ene-1-carboxylate; ethyl 2α,3γ-epoxy-2,6,6-trimethyl-cyclohexane-1β-carboxylate; ethyl 2β,3β-epoxy-2,6,6-trimethyl-cyclohexane-1β-carboxylate.

DESCRIPTION OF THE PREFERRED EMBODIMENTS

The process of the present invention utilizes an ester of 4-oxo-2,6,6-trimethylcyclohex-2-ene-1-carboxylic acid of the following structure as a starting material:

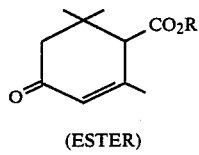

(ESTER)

wherein R is an aryl group or alkyl group having 1 to 6 carbon atoms. This compound is prepared by Lewis acid catalyzed condensation of an ester of acetoacetic acid and mesityl oxide or acetone. This ester may be converted to an olefin of the following structure:

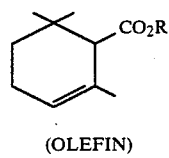

(OLEFIN)

by one of two methods. First, the above ester can be converted to a dithioketal of the following structures:

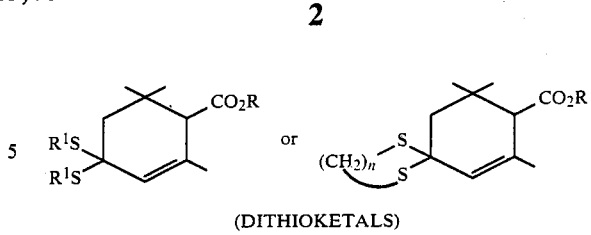

(DITHIOKETALS)

wherein $R^1$ is an aryl or alkyl group and n=2, 3, or 4.

These dithioketals are then desulfurized using Raney nickel or organosilane and Lewis acid to produce the olefin shown supra.

The above method is described by the following equation:

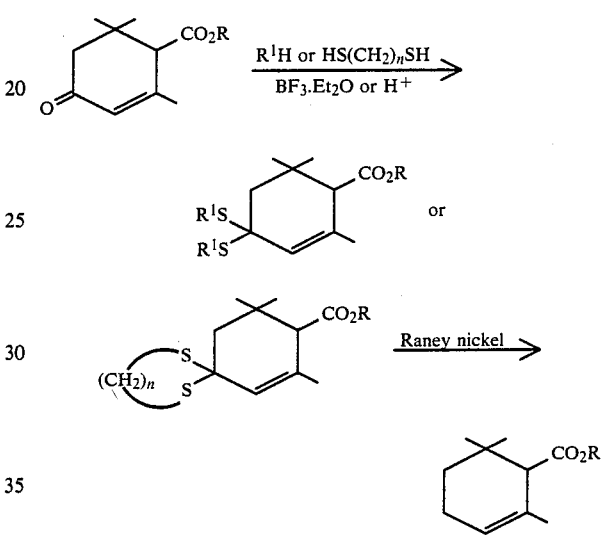

In the second method the same ester described supra is treated with a two to tenfold molar excess of a Lewis acid such as boron trifluoride etherate and a two to fivefold molar excess of an organosilane of the general structure of $R_2^2R^3SiH$ wherein ($R^2$ is alkyl, aryl, or alkoxy and $R^3$ is alkyl, aryl, alkoxy, or hydrogen) for a period of one hour to seven days at a temperature from about 20°–100° C.

This reaction can be represented by the following equation:

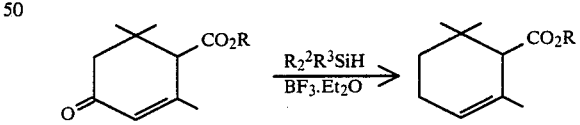

The present invention also includes enones of the general structure:

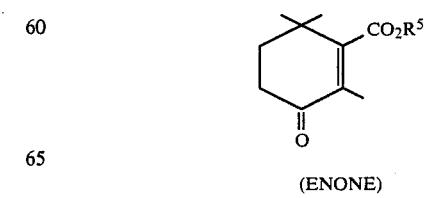

(ENONE)

produced by the following reactions:

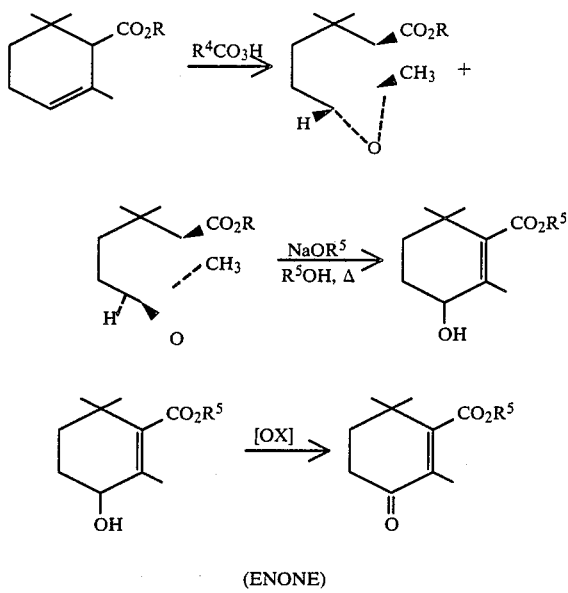

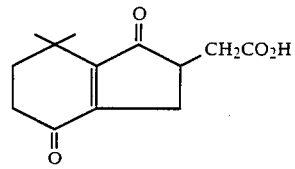

*NOTE:
Sequence of reaction.

In the above reaction sequence R⁴ is aryl or alkyl; R⁵ is an alkyl group having 1 to 6 carbon atoms.

The products of the first reaction are treated in an alcoholic solution with the corresponding alkoxide at 20° to 100° C. from about 1 to 24 hours to produce an allylic alcohol of the second reaction which is then converted to the enone of the third reaction by oxidizing with agents such as Jones reagent or activated manganese dioxide.

In addition, the enone can be used to prepare a bromoketone by reacting with N-bromosuccinimide (NBS) in carbon tetrachloride using light in the wavelengths of the visible range to initiate the reaction. No additional heat should be added to minimize the formation of side products. Generally, the reaction temperature is maintained at or below 50° C. This reaction can be represented by the following equation:

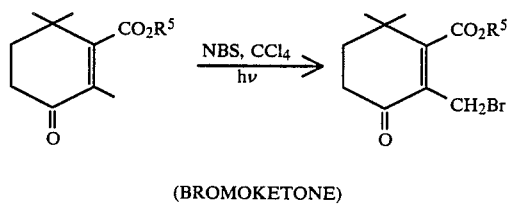

Subsequently, the bromoketone is converted to a diketo acid by the following reaction:

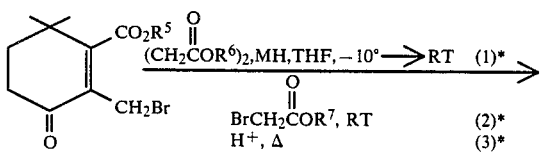

In the above reaction, M is Na or K; and, $R^6$ and $R^7$ can be methyl or ethyl.

In general, the anion of dimethyl malonate or diethyl malonate (1.1 to 2.0 equivalents) is generated in an inert ether such as diethyl ether or tetrahydrofuran (THF) or aromatic hydrocarbon (benzene, toluene) at $-10°$ C. to $+10°$ C. using sodium hydride or potassium hydride (2.2 to 4.0 equivalents) as base. After ten to thirty minutes, a solution of bromoketone (one equivalent) is added at $-10°$ C. to $+10°$ C. and the reaction mixture allowed to warm to room temperature. After one to eighteen hours, methyl or ethyl bromoacetate (1.3 to 2.7 equivalents) is added and the mixture stirred at room temperature for four to thirty hours after which a sufficient amount of acetic acid and dilute mineral acid is added to effect hydrolysis. The mixture is heated at reflux for $\frac{1}{2}$ to $1\frac{1}{2}$ hours and solvent is slowly distilled for 1 to 4 hours until the temperature of distillate reaches approximately 100° C. The diketo acid is then isolated from the undistilled acidic residue as described in Example 10 infra.

EXAMPLE 1

Preparation of Ethyl 4-Oxo-2,6,6-Trimethylcyclohex-2-Ene-1-Carboxylate

A mixture of 1020 ml (1041 g, 8.00 mol) of ethyl acetoacetate, 960 ml (824 g, 8.40 mol) of mesityl oxide, 1000 ml of heptane, 600 ml of toluene, and 175 g of zinc chloride was heated at reflux in a 5000 ml round bottom flask while stirring. The flask was equipped with a Dean-Stark trap and drying tube. After 24 h, an additional 25 g of zinc chloride was added and refluxing continued for 36 h. After cooling, the reaction mixture was washed with 1500 ml of water, 5% sodium bicarbonate solution (2×1000 ml), and another 1500 ml of water. Removal of solvent by evaporation yielded 979 g of crude product. Distillation of the crude product provided 453.5 g of the desired ester which represents 27.0% yield. Distillation was at 124°–5° C. (3.0 torr).

EXAMPLE 2

Preparation of 8-Carboethoxy-7,9,9-Trimethyl-1,4-Dithiosprio[4.5]-Dec-6-Ene

Boron trifluoride etherate (15 ml) was added to the ester of Example 1 (147.13 g, 0.700 mol) and 1,2-ethanedithiol (100 ml, 1.20 mol) and the mixture was stirred at 0° C. for 1 hr, then at 25° C. for 16 hr. The reaction mixture was poured into 1000 ml of 10% sodium hydroxide at 0°–5° C. and extracted with dichloromethane (3×500 ml). Combined organic extracts were washed with 500-ml portions of water and brine and dried over $MgSO_4$. Removal of solvent afforded 190 g of crude dithioketal which represents a 95% yield.

EXAMPLE 3

Preparation of Ethyl
2,6,6-Trimethylchlohex-2-Ene-1-Carboxylate

The dithioketal product of Example 2 (167.5 g, 0.585 mol), dissolved in 250 ml of ethanol, was added to a three liter two-neck flask equipped with mechanical stirrer. Raney nickel activated catalyst (500 g) was washed twice with 500 ml portions of ethanol and then added to the reaction flask with 1000 ml of ethanol. The reaction mixture was stirred at room temperature for 30 h. after which an additional 90 g of Raney nickel was added and stirring was continued for 90 h. The Raney nickel was removed by filtration and washed with ethanol (2×250 ml). Removal of solvent gave 130 g of residue which was partitioned between 300 ml of water and dichloromethane (2×300 ml). The combined organic layers were washed with 300 ml of brine and dried over MgSO$_4$. Removal of solvent afforded 112.8 g of product which was then distilled to give 27.4 g representing a 23.8% yield of olefin.

EXAMPLE 4

Direct Conversion of Ethyl
4-Oxo-2,6,6-Trimethylcyclohex-2-Ene-1-Carboxylate
to Ethyl 2,6,6-Trimethylcyclohex-2-Ene-1-Carboxylate A mixture of 20.0 g (95.1 mmol) of the reaction product of Example 1, 30.0 ml (244 mmol) of boron trifluoride etherate, and 39.0 ml (244 mmol) of triethylsilane was heated at 80°–95° C. for 2 h. After cooling, the reaction mixture was partitioned between 200 ml of dichloromethane and 100 ml of water. The layers were separated, and the aqueous layer was extracted with 500 ml of dichloromethane. The combined organic layers were washed with 100 ml portions of 10% sodium bicarbonate solution and brine. Distillation of the crude product through a 14-cm Vigreaux column afforded 12.26 g of desired olefin which represents a 65.7% yield.

EXAMPLE 5

Preparation of Ethyl 2α, 3α
Epoxy-2,6,6-Trimethylcyclohexane-1β-Carboxylate
and Ethyl 2β,
3β-Epoxy-2,6,6-Trimetyhylcyclohexane-1β-Carboxylate Sodium acetate (6.0 g) was added to 80 ml (0.419 mol) of 35% peracetic acid. The resulting mixture was added to a solution of 55.0 g (0.280 mol) of distilled olefin product of Example 4 in 400 ml of dichloromethane at 23° C. After 5 minutes, the temperature rose to 38° C. The reaction mixture was cooled at 20° C. over a 10 minute period. Stirring was continued at 20°–30° C. for 2 h. Following refrigeration at 0° C. overnight, the reaction mixture was washed with 250 ml of water, and the aqueous layer extracted with 200 ml of dichloromethane. Combined organic layers were washed with 250 ml portions of 10% sodium bicarbonate and brine and dried over MgSO$_4$. Removal of solvent gave 74.7 g of crude product.

EXAMPLE 6

Isolation of Ethyl 2α,
3α-Epoxy-2,6,6-trimethylcyclohexane-1β-Carboxylate
and Ethyl 2β,
3β-Epoxy-2,6,6-Trimethylcyclohexane-1β-Carboxylate A 4.18 g (21.3 mmol) sample of olefin from Example 4 was treated with a 50% excess of m-chloroperoxybenzoic acid (MCPBA) and yielded 4.81 g of crude product. The material was chromatographed on a column containing 200 g of silica gel. Elution with 3% ether/hexanes and 4% ether/hexanes afforded 0.61 g (13.5% yield) of ethyl 2β, 3β-epoxy-2,6,6-trimethylcyclohexane-1β-carboxylate. Continued elution of the column with 4%, 6%, 8%, and 10% ether/hexanes provided 2.58 g (57.1% yield) of ethyl 2α-3α-epoxy-2,6,6-trimethylcyclohexane-1β-carboxylate.

EXAMPLE 7

Preparation of Ethyl
3-Hydroxy-2-6,6-Trimethylcyclohex-1-Ene-1-Carboxylate

A solution of 1.59M sodium ethoxide (195 ml, 0.310 mol), prepared from 7.30 g of sodium and 200 ml of ethanol, was added to a stirred solution of 74.7 g of crude product of Example 5 (assumed to contain 0.28 mol of pure epoxides) under argon. The solution, which turned red, was heated under reflux for 1h. After cooling, the pH was adjusted to 6 by addition of 2.4M HCl (130 ml). Ethanol was removed in vacuo and the residue extracted with dichloromethane (2×250 ml). Combined organic layers were washed with 250 ml of brine and dried over MgSO$_4$. Removal of solvent furnished 69.35 g of crude allylic alcohol product.

EXAMPLE 8

Preparation of Ethyl
2,6,6-Trimethyl-3-Oxo-Cyclohex-1-Ene-1-Carboxylate

A 2.63M chromic acid solution was prepared from 30.5 g (0.305 mol) of chromium trioxide, 90 ml of water and 26 ml of concentrated sulfuric acid and was added dropwise over a 2 h period at 5° to 15° C. to a solution of 69.35 g of the crude product of Example 7 in 200 ml of acetone. The reaction mixture was allowed to stand at room temperature overnight. The reaction was completed by the addition of 0.50 ml of 2.64M chromic acid solution at 5° to 10° C. Isopropanol (5 ml) was added to destroy excess chromic acid and the bulk of the acetone was removed in vacuo. The residue was partitioned between water (200 ml) And ether (2×200 ml) following removal of the green solids by filtration. The ether solution was dried over MgSO$_4$ and evaporated to give 55.9 g of the pure enone product representing a 94.9% yield.

EXAMPLE 9

Preparation of Ethyl
2-Bromomethyl-6,6-Dimethyl-3-Oxo-Cyclohex-1-Ene-1-Carboxylate N-Bromosuccinimide (4.74 g, 26.8 mmol) was added to a solution of 4.67 g (22.2 mmol) of the enone product of Example 8 in 30 ml of carbon tetrachloride under argon. The stirred reaction mixture was irradiated with a 150-watt incandescent lamp at room temperature for 70 min., after which the mixture was filtered to remove solid succinimide. The filtrate was washed with 50 ml portions of 10% sodium sulfite solution and brine and dried over MgSO$_4$. Removal of solvent afforded 5.76 g of product which represents an 89.7% yield.

EXAMPLE 10

Preparation of 1-4-Dioxo-7,7-Dimethyl-4,5,6,7-Tetrahydro-2-Indanacetic Acid

Dimethyl malonate (3.3 ml, 29 mmol) was added to a mixture of 1.54 g (64 mmol) of sodium hydroxide and 50 ml of tetrahydrofuran (THF) under argon at 10° C. over a 15 minute period. The mixture was stirred at −10° C. for 20 min., after which a solution of 5.22 g (18.0 mmol) of product from Example 9 in 30 ml of THF was added dropwise over a 30 minute period. The mixture was stirred at −10° C. for ½ h, then at room temperature for 1½ h., after which 3.67 ml (3.9 mmol) of methyl bromoacetate was added. After 18 h at room temperature, the dark brown reaction mixture was treated with 30 ml of acetic acid and 30 ml of 6N HCl. The reaction mixture was heated with slow distillation of THF for 1 h, then at 90°-107° C. for 1 h. After cooling, the reaction mixture was partitioned between 30 ml of water and ethyl acetate (3×50 ml). The combined organic layers were extracted with 10% sodium carbonate solution (100 ml, 100 ml, 50 ml). The combined aqueous extracts were extracted with ether (100 ml) and then acidified with 40 ml of concentrated HCl and extracted with ethyl acetate (3×75 ml). Combined organic extracts were washed with 100 ml of brine and dried over MgSO4. Removal of solvent gave a viscous brown oil. Crystallization from ether provided 1.08 g of the reaction product representing a 25.3% yield.

I claim:

1. A process for preparing a compound which exhibits seed germinating activity comprising:
    (a) condensing an ester of acetoacetic acid with a ketone to produce a substituted cyclohexenone having the formula

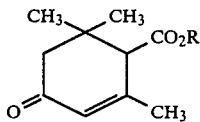

where R is an aryl group or alkyl group having 1 to 6 carbon atoms;
    (b) reacting the substituted cyclohexenone of (a) with a reducing agent comprising an organosilane and a Lewis acid sufficient to produce an ester of a substituted cyclohex-2-ene-1-carboxylic acid which exhibits seed germinating activity having the formula

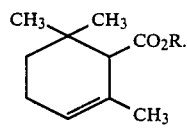

2. The process of claim 1 wherein the organosilane is selected from the group R²R³SiH wherein R² is alkyl, aryl, or alkoxy, and R³ is alkyl aryl, alkoxy, or hydrogen.

3. The process of claim 1 wherein the Lewis acid is boron trifluoride etherate.

4. The process of claim 1 including an additional step of reacting the product of step (b) with a peracid to produce epoxide isomers having the formulas

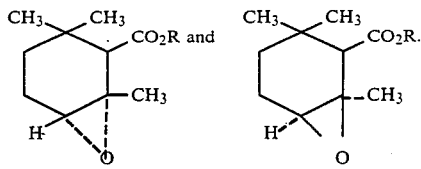

5. The process of claim 2 wherein the organosilane is triethylsilane.

6. The process of claim 4 wherein the peracid is peracetic acid.

7. The process of claim 4 wherein the epoxide isomers produced are selected from the group consisting of: ethyl 2α,3α-epoxy-2,6,6-trimethylcyclohexane-1β-carboxylate, and ethyl 2β,3β-epoxy-2,6,6-trimethycyclohexane-1β carboxylate.

8. The process of claim 7 including the additional step of treating the epoxide isomers with an alkoxide having an alkyl group with 1 to 6 carbon atoms which will produce an allylic alcohol which exhibits seed germinating activity and having the formula

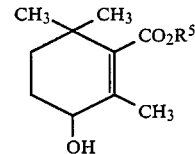

wherein R⁵ is an alkyl group having 1 to 6 carbon atoms.

9. The process of claim 8 including the additional step of oxidizing the allylic alcohol to produce an enone which exhibits germinating activity and having the formula

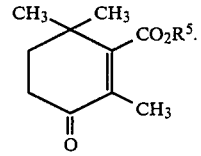

10. The process of claim 9 wherein the allylic alcohol is ethyl 3-hydroxy-2,6,6-trimethylcyclohex-1-ene-1carboxylate and the enone is ethyl 2,6,6-trimethyl-3-oxocyclohex-1-ene-1-carboxylate.

11. The process of claim 9 including the step of brominating the enone to produce a 2-bromomethyl-6,6-dimethylcyclohex-1-ene-1-carboxylate which exhibits seed germinating activity.

12. The process of claim 11 wherein the 2-bromomethyl compound is ethyl 2-bromomethyl-6,6-dimethyl-3-oxo-cyclohex-1-ene-1-carboxylate.

13. The process of claim 11 including the additional steps of: reacting the bromomethyl compound with an anion of an ester of malonic acid; then adding an ester of bromoacetic acid; and then hydrolyzing with a mixture of acetic acid and dilute mineral acid at a temperature from about 50° to 100° C. for sufficient time to produce 1,4-dioxo-7,7-dimethyl-4,5,6,7-tetrahydro-2-indanacetic acid which exhibits seed germinating activity.

14. The process of claim 13 wherein the ester of malonic acid is selected from the group: dimethyl malonate and diethyl malonate.

15. The process of claim 13 wherein the ester of bromoacetic acid is selected from the group: methyl bromoacetate and ethyl bromoacetate.

16. The process of claim 13 wherein the mineral acid is hydrochloric acid.

17. A process comprising reacting a first material having the formula

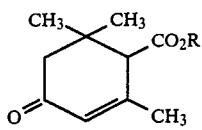

with an organosilane and a Lewis acid to produce an olefin having the formula

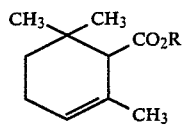

where R is an aryl group or alkyl ester group having 1 to 6 carbon atoms.

18. The process of claim 17 further comprising reacting said olefin with a peracid to produce epoxide isomers having the formula

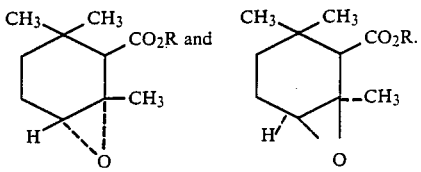

19. The process of claim 18 further comprising reacting said epoxide isomers with an alkoxide having an alkyl group with 1 to 6 carbon atoms to produce an allylic alcohol having the formula

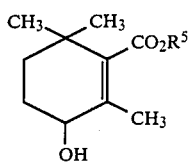

where $R^5$ is an alkyl group having 1 to 6 carbon atoms.

20. The process of claim 19 further comprising oxidizing said allylic alcohol to produce an enone having the formula

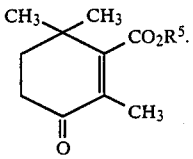

21. The process of claim 20 further comprising brominating said enone to produce a 2-bromomethyl-6,6-dimethylcyclohex-1-ene-1-carboxylate.

22. The process of claim 21 further comprising reacting said bromomethyl compound with an anion of an ester of malonic acid; then adding an ester of bromoacetic acid; and then hydrolyzing with a mixture of acetic acid and dilute mineral acid to produce 1,4-dioxo-7,7-dimethyl-4,5,6,7-tetrahydro-2-indanacetic acid.

* * * * *